United States Patent
Ooms et al.

(10) Patent No.: US 6,600,064 B2
(45) Date of Patent: Jul. 29, 2003

(54) PROCESS FOR THE PREPARATION OF HYDROXYBENZOIC BENZYL ESTERS

(75) Inventors: Pieter Ooms, Krefeld (DE); Bernd-Ulrich Schenke, Bottrop (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/090,392

(22) Filed: Mar. 4, 2002

(65) Prior Publication Data

US 2002/0128523 A1 Sep. 12, 2002

(30) Foreign Application Priority Data

Mar. 7, 2001 (DE) .......................... 101 10 746

(51) Int. Cl.$^7$ ........................ C07C 69/76; C07C 67/24
(52) U.S. Cl. ......................... 560/61; 560/240
(58) Field of Search .................. 560/61, 240

(56) References Cited

PUBLICATIONS

Encyclopedia of Polymer Science and Technology, vol. 7, (month unavailable) 1967), pp. 692–705, "Ion–Exchange Polymers".

Chemical Reviews, 98, (month unavailable) 1998, pp. 3–49, Louis C.W. Baker & Diana C. Glick, "Present General Status of Understanding of Heteropoly Electrolytes and a Tracing of Some Major Highlights in the History of Their Elucidation".

Catal. Rev.–Sci. Eng., 37(2), (month unavailable) 1995, pp. 311–352, Ivan V. Kozhevnikov "Heteropoly Acids and Related Compounds as Catalysts for Fine Chemical Synthesis".

Kumarapuram N. Parameswaran et al.: "O–Carbamoylsalicylates: Agents for modification of Hemoglobins" J. Med Chem., Bd. 30, 1987, Seite 936–939 XP001071247 * Seite 938, letzter Absatz—Seite 939 *.

Chen et al: Structure–Activity Relationships in a Series of 5–'(2,5–Dihydroxybenzyl)amino!salicylate Inhibitors of EGF–Receptor– Associated Tyrosine Kinase: Importance of Additional Hydrophobic Aromatic Interactions: Journal of Medicinal Chemistry, American Chemical Society. Washington, US, Bd. 37, Nr. 6, 1994, Seiten 845–859, XP002127746 ISSN: 0022–2623 *Seite 847, Scheme 3, Herstellung von A24, A31 und A32 aus Tabelle 1 *.

Ullmann's Encyclopedia of Industrial Chemistry, $5^{th}$ edition, vol. B4, (month unavailable) 1998, pp. 568–570, Editors Barbara Elvers, Stephen Hawkins, Gail Schulz, "Continuous Mixing of Fluids".

Ullmann's Encyclopedia of Industrial Chemistry $5^{th}$ edtion, B2, Section 25, (month unavailable) 1988, pp. 1–33,Marko Zlokarnik, Helmut Judat, Stirring.

Ullmann'Encyclopedia of Industrial Chemistry, $5^{th}$ edition, B2, Section 26, (month unavailable) 1988, pp. 1–16, David B. Todd, "Mixing of Highly Viscous Media".

*Primary Examiner*—Richard L. Raymond
*Assistant Examiner*—Zachary C. Tucker
(74) *Attorney, Agent, or Firm*—Godfried R. Akorli; Diderico van Eyl

(57) ABSTRACT

The invention relates to a process for the preparation of hydroxybenzoic benzyl esters by reacting dibenzyl ethers with alkylcarbonyloxybenzoic or alkoxycarbonyloxybenzoic acids and optionally anhydrides thereof in the presence of one or more acids as catalyst.

21 Claims, No Drawings

PROCESS FOR THE PREPARATION OF HYDROXYBENZOIC BENZYL ESTERS

BACKGROUND OF THE INVENTION

The present invention relates to a process for the preparation of hydroxybenzoic benzyl esters by reacting dibenzyl ethers with alkylcarbonyloxybenzoic or alkoxycarbonyloxybenzoic acid in the molar ratio 1:1 to 1:50 at 10 to 200° C. and pressures in the range from 0.1 to 50 bar in the presence of acid as catalyst.

Benzyl salicylate is used as stabilizer in fragrance compositions and sunscreens. Benzyl salicylate and processes for its preparation are already known.

Thus, EP-A 117,502 describes, for example, the preparation of benzyl salicylate by esterifying salicylic acid or transesterifying salicylic esters with benzyl alcohol.

Benzyl salicylate can also be prepared by reacting alkali metal salicylates with benzyl chloride, optionally in the presence of phase-transfer reagents (JP 63/218652, EP-A 534,817). A disadvantage is the formation of salts that must be disposed of and thus reduce the economic feasibility of these processes.

The object was to develop a process, starting from dibenzyl ethers, for the preparation of hydroxybenzoic benzyl esters that can be carried out under mild reaction conditions and leads to good yields in a cost-effective manner.

SUMMARY OF THE INVENTION

The present invention relates to a process for the preparation of hydroxybenzoic benzyl esters of the formula

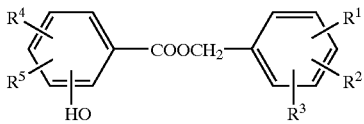

in which
$R^1$ to $R^5$ are identical or different and are $C_1$–$C_6$-alkyl, $C_1$–$C_6$-alkoxy-, $C_1$–$C_6$-halogenoalkyl, $C_1$–$C_6$-halogenoalkoxy-, CN, CO($C_1$–$C_6$-alkyl), $NO_2$, or halogen, comprising reacting dibenzyl ethers of the formula

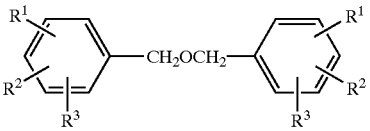

in which
$R^1$, $R^2$, and $R^3$ are as defined above,
or mixtures of such dibenzyl ethers and benzyl alcohols of the formula

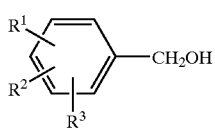

in which
$R^1$, $R^2$, and $R^3$ are as defined above, with alkylcarbonyloxybenzoic or alkoxycarbonyloxybenzoic acids of the formula

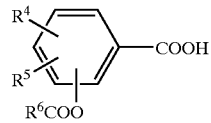

in which
$R^4$ and $R^5$ are as defined above and
$R^6$ is hydrogen or a straight-chain or branched, saturated or unsaturated, optionally halogen-substituted alkyl, aralkyl, aryl, alkoxy, aralkoxy, or aryloxy group having 1 to 50 carbon atoms,
in the presence of one or more acids as catalyst.

DETAILED DESCRIPTION OF THE INVENTION

The process according to the invention can be carried out in a cost-effective manner and under mild reaction conditions.

The radicals $R^1$ to $R^5$ are generally defined as follows:

Alkyl generally means a straight-chain or branched hydrocarbon radical having 1 to 6 (preferably 1 to 4, particularly preferably 1 or 2) carbon atoms. For example, mention may be made of methyl, ethyl, propyl, isopropyl, butyl, isobutyl, pentyl, isopentyl, hexyl, and isohexyl. Preference is given to methyl and ethyl.

Alkoxy generally means a straight-chain or branched alkoxy radical having 1 to 6 (preferably 1 to 4, particularly preferably 1 or 2) carbon atoms. For example, mention may be made of methoxy, ethoxy, propoxy, isopropoxy, butoxy, isobutoxy, pentoxy, isopentoxy, hexoxy, and isohexoxy. Preference is given to methoxy and ethoxy.

Halogenoalkyl generally means a straight-chain or branched hydrocarbon radical having 1 to 6 (preferably 1 to 4, particularly preferably 1 or 2) carbon atoms having 1 to 10 (preferably 1 to 8, particularly preferably 1 to 5) halogen atoms. For example, mention may be made of chloromethyl, fluoromethyl, trifluoromethyl, fluoroethyl, fluoropropyl, and hexafluorobutyl. Preference is given to fluoromethyl and trifluoromethyl.

Halogenoalkoxy generally means a straight-chain or branched alkoxy radical having 1 to 6 (preferably 1 to 4, particularly preferably 1 or 2) carbon atoms having 1 to 10, preferably 1 to 8, particularly preferably having 1 to 5, halogen atoms. For example, mention may be made of chloromethoxy, fluoromethoxy, trifluoromethoxy, fluoroethoxy, fluoropropoxy, and hexa-fluorobutoxy. Preference is given to fluoromethoxy and trifluoromethoxy.

Halogen generally means fluorine, chlorine, bromine, or iodine, preferably fluorine or chlorine.

Preferred substituents for $R^1$ to $R^5$ are methyl, trifluoromethyl, methoxy, fluorine, or chlorine.

Alkyl, aralkyl, aryl, alkoxy, aralkoxy, and aryloxy groups (i.e., for $R^6$) generally comprise 1 to 50 carbon atoms, preferably 1 to 10 carbon atoms.

The following hydroxybenzoic benzyl esters can, for example, be prepared by the process according to the invention: benzyl 2-hydroxybenzoate (benzyl salicylate); benzyl 3-hydroxybenzoate, benzyl 4-hydroxybenzoate; benzyl 3-chloro-2-hydroxybenzoate, benzyl 4-chloro-2-hydroxybenzoate, benzyl 5-chloro-2-hydroxybenzoate; benzyl 6-chloro-2-hydroxybenzoate; benzyl 3-bromo-2- hydroxybenzoate, benzyl 3-fluoro-2-hydroxybenzoate, benzyl 4-fluoro-2-hydroxybenzoate, benzyl 2-fluoro-3-hydroxybenzoate, benzyl 2-fluoro4-hydroxybenzoate; benzyl 3-fluoro-2-hydroxybenzoate, benzyl 2-fluoro-5-hydroxybenzoate, benzyl 2-fluoro-6-hydroxybenzoate, benzyl 2-hydroxy-3-methylbenzoate, benzyl 2-hydroxy-4-methylbenzoate, benzyl 3-hydroxy-2-methylbenzoate, benzyl 4-hydroxy-2-methylbenzoate, benzyl 2-fluoro-6-hydroxy4-methoxybenzoate, benzyl 3-trifluoromethyl-2-hydroxybenzoate, benzyl 4-trifluoromethyl-2-hydroxybenzoate, benzyl 2-trifluoromethyl-3-hydroxybenzoate, benzyl 2-fluoroethyl-4-hydroxybenzoate, and benzyl 4-fluorobutyl-2-hydroxybenzoate.

The dibenzyl ether used in the process according to the invention is unsubstituted dibenzyl ether or a substituted dibenzyl ether. Particular preference is given to using unsubstituted dibenzyl ether.

In the process according to the invention, it is possible to use dibenzyl ethers or dibenzyl ether/benzyl alcohol mixtures as are formed, for example, in the preparation of benzyl alcohol from benzyl chloride. The content of dibenzyl ether in the mixture can be 50 to 100% by weight, preferably 60 to 99% by weight, particularly preferably 70 to 98% by weight.

For the process according to the invention, mention may be made, for example, of the following alkylcarbonyloxybenzoic and alkoxycarbonyl oxybenzoic acids: 2-formyloxybenzoic acid, 3-formyloxybenzoic acid, 4-formyloxybenzoic acid, 2-acetoxybenzoic acid, (2-acetylsalicylic acid); 3-acetoxybenzoic acid, 4-acetoxybenzoic acid, 2-propionyloxybenzoic acid, 2-butyryloxybenzoic acid, 2-benzoyloxybenzoic acid, 2-acetoxy-3-chloro benzoic acid, 2-acetoxy-4-chlorobenzoic acid, 2-acetoxy-5-chlorobenzoic acid, 2-acetoxy-6-chlorobenzoic acid, 2-acetoxy-3-bromobenzoic acid, 2-acetoxy-3-chlorobenzoic acid, 2-formyloxy-3-fluorobenzoic acid, 2-acetoxy-3-fluorobenzoic acid, 2-acetoxy4-fluorobenzoic acid, 3-acetoxy-2-fluorobenzoic acid, 2-fluoro4-propionyloxybenzoic acid, 2-butyroxy-3-fluorobenzoic acid, 2-fluoro-5-hydroxybenzoic acid, 6-acetoxy-2-fluorobenzoic acid, 2-acetoxy-3-methylbenzoic acid, 2-acetoxy-4-methylbenzoic acid, 3-acetoxy-2-methylbenzoic acid, 4-acetoxy-2-methylbenzoic acid, 6-acetoxy-2-fluoro4-methoxybenzoic acid, 2-acetoxy-3-trifluoromethyl-benzoic acid, 2-acetoxy4-trifluoromethylbenzoic acid, 3-acetoxy-2-trifluoromethyl-benzoic acid, 4-acetoxy-2-fluoroethylbenzoic acid, 2-acetoxy-4-fluorobutyl-benzoic acid, 2-methoxycarbonyloxybenzoic acid, 2-ethoxycarbonyloxybenzoic acid, 3-methoxycarbonyloxybenzoic acid, or trifluoroacetoxybenzoic acid.

Preference is given to alkylcarbonyloxybenzoic and alkoxycarbonyloxybenzoic acids having 2 to 30 carbon atoms, particularly preferably 2 to 12 carbon atoms. Very particular preference is given alkylcarbonylsalicylic acids.

The process according to the invention is preferably carried out with removal of the water that is formed. It is appropriate to remove the water by distillation or by passing through an inert gas, such as, for example, nitrogen. To remove the water that is formed, preference is given to using water-withdrawing agents, for example, zeolites, aluminum oxides, or clay earths. Particular preference is given to removing the water that is formed by carrying out the reaction in the presence of the corresponding anhydride of the alkylcarbonyloxybenzoic or alkoxycarbonyloxybenzoic acid used as water-withdrawing agent. Very particularly preferred anhydrides are acetylsalicylic anhydrides.

In the process according to the invention, preference is given to using 0.5 to 50 mol of alkylcarbonyloxybenzoic or alkoxycarbonyloxybenzoic acid (preferably 1 to 30 mol, particularly preferably 2 to 20 mol), based on dibenzyl ether.

If the process according to the invention is carried out in the presence of the corresponding anhydride of the alkylcarbonyloxybenzoic or alkoxycarbonyloxybenzoic acid, then 0.1 to 10 mol of anhydride (preferably 0.5 to 7.5 mol, particularly preferably 1 to 5 mol), based on dibenzyl ether, are preferably used. Since one molecule of anhydride reacts, with the uptake of water, to give 2 molecules of carboxylic acid, it is possible to use smaller amounts of carboxylic acid in the process according to the invention. Preferably, 0.25 to 25 mol (preferably 0.5 to 15 mol, particularly preferably 1 to 10 mol) of carboxylic acid, based on dibenzyl ether, are then used.

In the process according to the invention, acids are used either as homogeneous or as heterogeneous catalysts.

The acids used as catalyst for the process according to the invention generally have a pH of from 1 to 6, preferably from 1 to 5, particularly preferably from 1 to 4.

Suitable catalysts for the process according to the invention are inorganic acids, such as, for example, sulfuric acid, hydrochloric acid, hydrobromic acid, hydroiodic acid, hydrofluoric acid, perchloric acid, chlorosulfonic acid, or phosphoric acid, organic acids, such as, for example, trifluoroacetic acid, methanesulfonic acid, ethanesulfonic acid, benzenesulfonic acid, 4-toluenesulfonic acid, or trifluoromethanesulfonic acid, and Lewis acids, such as, for example, boron trifluoride, aluminum chloride, aluminum bromide, aluminum iodide, zinc chloride, tin chloride, titanium chloride, or zirconium chloride.

Preference is given to sulfuric acid, trifluoromethanesulfonic acid, 4-toluenesulfonic acid, and boron trifluoride, particularly preferably sulfuric acid, trifluoromethanesulfonic acid, and boron trifluoride.

The acids can either be used as homogeneous catalyst or else on an inert support as a heterogeneous catalyst.

In the process according to the invention, the heterogeneous acidic catalysts are preferably acidic ion exchangers, such as, for example, sulfonylated polymers, such as sulfonylated polystyrenes, sulfonylated styrene divinylbenzene copolymers, and sulfonylated phenol-formaldehyde resins.

Preference is given to sulfonylated polystyrenes and sulfonylated styrene-divinylbenzene copolymers, particularly preferably sulfonylated polystyrenes.

The ion exchangers are obtainable by reacting polystyrene or styrene-divinylbenzene copolymers with sulfonation agents such as sulfuric acid or chlorosulfonic acid.

Methods for the preparation are well known and described, for example, in Encyclopedia of Polymer Science and Technology, 1967, Volume 7, pp. 692 to 705.

Standard commercial ion exchangers, such as, for example, products sold under the registered trade names Lewatit, Amberlyst, Amberlite, Dowex, Duolite, Nafion, Permutit, Chempro, and Imac, are suitable.

The ion exchangers can be in spherical form and have particle sizes of from 0.3 to 3.0 mm in diameter. The ion exchangers can be of the gel type or macroporous. Their total capacity of acid functions in water-moist form with a water content of from about 75 to 85% by weight ranges from 0.7 to 2.1 mval/ml of ion exchanger or from 3.5 to 5 mval/ml, based on 1 g of dry substance of ion exchanger.

The ion exchangers are, where appropriate, dried by heat, optionally under reduced pressure, optionally by washing with hydrophilic organic liquids, such as, for example, the carboxylic acid used or the carboxylic anhydride used, or optionally by azeotropic distillation with organic liquids such as toluene, xylene, or methylene chloride.

Such ion exchangers are used, when working with suspended catalysts in stirred vessels, in amounts of from 0.1 to 100% by weight (preferably from 0.5 to 90% by weight and particularly preferably from 1.0 to 80% by weight), based on dibenzyl ether.

In the case of a continuous procedure in countercurrent or cocurrent or in the trickle phase on a fixed-bed catalyst, space velocities of from 0.05 g to 5000 g of dibenzyl ether per liter of swollen ion exchanger per hour, preferably from 0.1 to 4000 g/l h and particularly preferably from 1.0 to 3000 g/l h.

In a particular embodiment of the process according to the invention, the catalysts are heteropolyacids (polyoxymetallates) of the general formula

$$H_a X_b M_c O_d$$

in which

H is hydrogen and/or metal cations,

X is phosphorus, silicon, boron, or germanium,

M is tungsten, molybdenum, vanadium, or chromium, a is 3, 4, 5, or 6, with the proviso that the heteropolyacids or salts thereof have electroneutrality, b is 1 or 2, c is 12 or 18, and d is 40 or 62.

Metal cations that may be mentioned are alkali metals such as lithium, sodium, potassium, rubidium, or cesium or manganese, nickel, cobalt, copper, or lanthanum.

Preference is given to heteropolyacids of the Keggin type (Chem. Rev. 98 (1998) p.12), i.e., compounds in which b=1, c=12, and d=40, where X is hydrogen.

Preference is given to molybdenum, tungsten, and vanadium oxides with phosphoric acid or silicic acid, such as, for example, phosphotungstic acid, silicotungstic acid, phosphomolybdic acid, silicomolybdic acid, phosphovanadic acid, and silicovanadic acid. Particular preference is given to phosphotungstic acid, silicotungstic acid, phosphomolybdic acid, and silicomolybdic acid.

Methods for the preparation are well known and are described, for example, in Römpp Lexikon Chemie, 10th edition, Stuttgart/N.Y., 1997, volume 3, p. 1741, and Chemical Reviews 98, (1998), pp. 3–49, Catal. Rev.-Sci Eng., 37,311 to 321 (1995).

The heteropolyacids, and where appropriate hydrates thereof, can be used either as homogeneous catalyst or else on an inert support as heterogeneous catalyst.

The catalysts can, for example, be used as powders or molded bodies and be separated off after the reaction, for example, by filtration, sedimentation, or centrifugation.

In the case of the arrangement as a fixed bed, the catalysts are preferably applied to a support and used as molded bodies, e.g., as spheres, cylinders, rods, hollow cylinders, rings, etc. Suitable support materials are activated carbon, silica gel, aluminum oxide, aluminosilicates such as zeolites or phyllosilicates, clay earths, titanium oxides, and zirconium oxides.

These heterogenized catalysts are optionally dried by heating, where appropriate under reduced pressure, where appropriate by washing with hydrophilic organic liquids, such as, for example, the carboxylic acid used or the carboxylic anhydride used, or where appropriate by azeotropid distillation with organic liquids such as toluene, xylene, or methylene chloride.

When working with suspended catalysts in stirred vessels, the acids are used in amounts of from 0.1 to 100% by weight)preferably from 0.5 to 90% by weight and particularly preferably from 1.0 to 80% by weight), based on dibenzyl ether.

In the case of a continuous procedure in countercurrent or cocurrent or in the trickle phase over a fixed-bed catalyst, space velocities of from 0.05 g to 5000 g of dibenzyl ether per liter of immobilized acid per hour (preferably from 0.1 to 4000 g/l h and particularly preferably from 1.0 to 3000 g/l h), are used.

The process according to the invention is preferably carried out with intensive mixing of the reactants. Intensive mixing can be achieved in various ways known to the person skilled in the art, for example by stirrers, nozzles, baffles, static mixers, pumps, turbulent flows in narrow tubes, and ultrasound. Such devices are described in more detail in Ullmann's Encyclopedia of Industrial Chemistry, 5th edition, volume B, Unit Operations, sections 25, 26, B4 pp. 568–570, Verlag Chemie, Weinheim 1988.

A preferred embodiment of the process according to the invention involves adding dibenzyl ether to a mixture or suspension of acid, optionally deposited on a support, and alkylcarbonyloxybenzoic or alkoxycarbonyloxybenzoic acid and anhydride, and when the reaction is complete, separating off the catalyst by, for example, filtration or centrifugation.

A further preferred embodiment is the cocurrent procedure in which dibenzyl ether and alkylcarbonyloxybenzoic or alkoxycarbonyloxybenzoic acid and anhydride are passed cocurrently, for example, from the top downwards, over a catalyst bed arranged in a tube, and benzyl hydroxybenzoates are drawn off at the bottom at the foot of the tube.

In a further preferred embodiment of the process according to the invention, this is carried out in the trickle phase and the heterogeneous catalyst (preferably a supported acid) is in the form of a fixed-bed catalyst. The catalyst bed is preferably in a perpendicular tubular reactor that preferably contains intermediate plates to improve distribution of the liquid stream and to improve wetting of the catalyst bed.

Both in the case of the suspended catalyst and also in the case of fixed-bed process variants, work-up may be carried out by adding a water-immisicible solvent (preferably toluene) to the reaction products. Following removal of the organic phase, which comprises the crude hydroxybenzoic benzyl ester, the organic phase can be further purified, for example, by distillation.

The process according to the invention can be carried out batchwise, continuously or semicontinuously.

The temperature at which the process according to the invention is carried out is preferably 15 to 200, particularly preferably 25 to 190, very particularly preferably 30 to 180° C.

If the reaction is carried out above 115° C., it is necessary to work under increased pressure, corresponding to the vapor pressure. The required gauge pressure is then at least equal to the vapor pressure of the reaction mixture. The pressure may be up to about 50 bar, preferably up to 25 bar.

Where appropriate, the process according to the invention can be carried out under a customary protective gas, such as, for example, nitrogen, helium, or argon.

The process according to the invention can be illustrated by the following reaction equation:

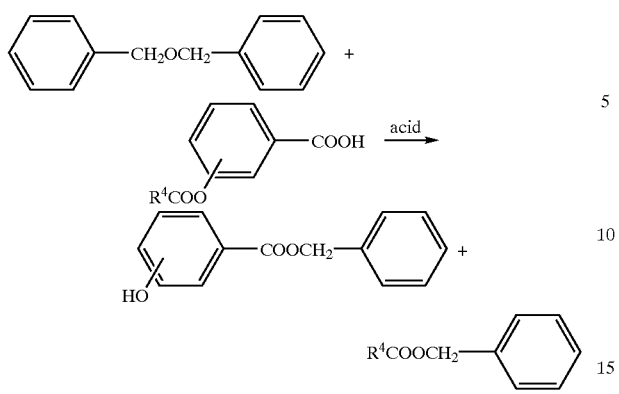

The process according to the invention gives hydroxybenzoic benzyl esters in good yields with a high conversion and good selectivity. The process according to the invention can be carried out easily without high expenditure on apparatus.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. The percentages given in the examples below refer to the weight.

EXAMPLES

Example 1

49.6 g (0.25 mol) of dibenzyl ether, 45.0 g (0.25 mol) of 2-acetoxybenzoic acid (2-acetylsalicylic acid) (Acros), and 0.25 g of concentrated sulfuric acid (Riedel-de Haen) were heated at 120° C. in a flask with baffles and paddle stirrer with vigorous stirring (250 rpm) and under nitrogen. After a reaction time of 3 hours, the mixture was cooled rapidly, and, following the addition of toluene and water, the organic phase was separated off and analyzed using gas chromatography. The reaction mixture comprised dibenzyl ether/benzyl salicylate/benzyl acetate/2-acetylbenzyl salicylate in the ratio 1.8:40.2:37.3:2.4, corresponding to a conversion of dibenzyl ether of 98%.

Example 2

Example 1 was repeated, but using 0.5 g of concentrated sulfuric acid (Riedel-de Haen). After 0.5 hours, the reaction mixture comprised dibenzyl ether/benzyl salicylate/benzyl acetate/2-acetylbenzyl salicylate in the ratio 0.2:37.5:33.6:1.7, corresponding to a conversion of 99%.

Example 3

Example 1 was repeated, but using 90.0 g (0.5 mol) of 2-acetoxybenzoic acid and 0.5 g of concentrated sulfuric acid (Riedel-de-Haen) at 90° C. After a reaction time of 5 hours, the reaction mixture comprised dibenzyl ether/benzyl salicylate/benzyl acetate/2-acetylbenzyl salicylate in the ratio 6.2:17.6:25.5:25.0, corresponding to a conversion of 93%.

Example 4

Example 1 was repeated, but using 0.1 g of trifluoromethanesulfonic acid (Acros) at 90° C. After a reaction time of 0.5 hours, the reaction mixture comprised dibenzyl ether/benzyl salicylate/benzyl acetate/2-acetylbenzyl salicylate in the ratio 6.9:26.5:36.1:1.1, corresponding to a conversion of 93%.

Example 5

Example 1 was repeated, but using 0.25 g of trifluoromethanesulfonic acid zinc salt (Fluka). After a reaction time of 1 hour, the reaction mixture comprised dibenzyl ether/benzyl salicylate/benzyl acetate/2-acetylbenzyl salicylate in the ratio 10.3:28.6:33.4:2.2, corresponding to a conversion of 87%.

Example 5

Example 1 was repeated, but using 0.5 g of boron trifluoride dietherate (Fluka). After a reaction time of 7 hours, the reaction mixture comprised dibenzyl ether/benzyl salicylate/benzyl acetate/2-acetylbenzyl salicylate in the ratio 15.7:30.6:32.2:11.9, corresponding to a conversion of 81%.

Example 6

Example 1 was repeated, but using 0.25 g phosphomolybdic acid (Aldrich). After a reaction time of 1 hour, the reaction mixture comprised dibenzyl ether/benzyl salicylate/benzyl acetate/2-acetylbenzyl salicylate in the ratio 68.7:3.5:5.0:3.5, corresponding to a conversion of 9%.

Example 7

Example 1 was repeated, but using 0.25 g of a sulfonylated styrene-divinylbenzene copolymer Lewatit® SC 102 (Bayer). After a reaction time of 1 hour, the reaction mixture comprised dibenzyl ether/benzyl salicylate/benzyl acetate/2-acetylbenzyl salicylate in the ratio 7.1:16.9:21.9:0.3, corresponding to a conversion of 92%.

What is claimed is:

1. A process for the preparation of hydroxybenzoic benzyl esters of the formula

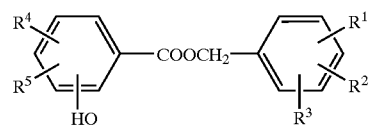

in which $R^1$ to $R^5$ are identical or different and are $C_1$–$C_6$-alkyl, $C_1$–$C_6$-alkoxy-, $C_1$–$C_6$-halogenoalkyl, $C_1$–$C_6$-halogenoalkoxy-, CN, CO($C_1$–$C_6$-alkyl), $NO_2$, or halogen, comprising reacting a dibenzyl ether of the formula

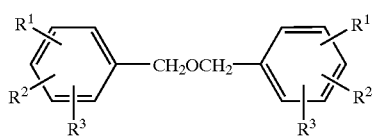

in which $R^1$, $R^2$, and $R^3$ are as defined above, or a mixture of such dibenzyl ether and a benzyl alcohol of the formula

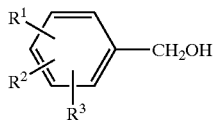

in which
R$^1$, R$^2$, and R$^3$ are as defined above,
with an alkylcarbonyloxybenzoic or alkoxycarbonyloxybenzoic acid of the formula

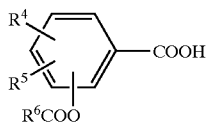

in which
R$^4$ and R$^5$ are as defined above and
R$^6$ is hydrogen or a straight-chain or branched, saturated or unsaturated, optionally halogen-substituted alkyl, aralkyl, aryl, alkoxy, aralkoxy, or aryloxy group having 1 to 50 carbon atoms,
in the presence of one or more acids as catalyst.

2. A process according to claim 1 wherein the acid is an inorganic acid, organic acid, or Lewis acid with a pH value of from 1 to 6.

3. A process according to claim 1 wherein the acid is an acidic ion exchanger.

4. A process according to claim 3 wherein the acidic ion exchanger is a sulfonylated polymer.

5. A process according to claim 3 wherein the acidic ion exchanger is a fluorinated or perfluorinated sulfonylated polymer, a fluorinated or perfluorinated sulfonylated styrene-divinylbenzene copolymer, and/or a fluorinated or perfluorinated sulfonylated phenol-formaldehyde resin.

6. A process according to claim 1 wherein the acid is a heteropolyacid of the formula $$H_a X_b M_c O_d$$

in which
H is hydrogen and/or metal cations,
X is phosphorus, silicon, boron, or germanium,
M is tungsten, molybdenum, vanadium, or chromium,
a is 3, 4, 5, or 6, with the proviso that the heteropolyacids or salts thereof have electroneutrality,
b is 1 or 2,
c is 12 or 18, and
d is 40 or 62.

7. A process according to claim 6 wherein the heteropolyacid is phosphotungstic acid, silicotungstic acid, phosphomolybdic acid, or silicomolybdic acid.

8. A process according to claim 1 wherein the dibenzyl ether is unsubstituted.

9. A process according to claim 1 wherein the dibenzyl ether is a substituted dibenzyl ether of the formula

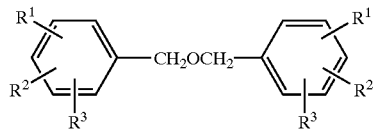

in which R$^1$ to R$^3$ are identical or different and are C$_1$–C$_6$-alkyl, C$_1$–C$_6$-alkoxy-, C$_1$–C$_6$-halogenoalkyl, C$_1$–C$_6$-halogenoalkoxy-, CN, CO(C$_1$–C$_6$-alkyl), NO$_2$, or halogen.

10. A process according to claim 1 wherein 0.5 to 50 mol of an acyloxybenzoic acid, based on dibenzyl ether, are used.

11. A process according to claim 1 wherein the reaction is carried out in the presence of a water-withdrawing agent.

12. A process according to claim 1 wherein the reaction is carried out with the removal of water by distillation or by passing through nitrogen.

13. A process according to claim 1 wherein the reaction is carried out in the presence of an anhydride corresponding to the alkylcarbonyloxybenzoic or alkoxycarbonyloxybenzoic acid.

14. A process according to claim 13 wherein 0.1 to 10 mol of the anhydride, based on dibenzyl ether, are used.

15. A process according to claim 1 carried out in a temperature range of from 15 to 200° C.

16. A process according to claim 1 wherein the acid is selected from the group consisting of inorganic, organic, and Lewis acids and is used in an amount of from 0.05 to 10% by weight, based on the amount of the dibenzyl ether.

17. A process according to claim 1 wherein the acid is selected from the group consisting of inorganic, organic, and Lewis acids arranged as a fixed bed and is used with space velocities of from 1.0 to 3000 g per liter of heterogenized acid per hour.

18. A process according to claim 3 wherein one or more acidic ion exchangers selected from the group consisting of optionally fluorinated, sulfonylated polystyrenes, optionally fluorinated or perfluorinated, sulfonylated styrene-divinylbenzene copolymers, and optionally fluorinated or perfluorinated sulfonylated phenol-formaldehyde resins are used as a suspended catalyst in an amount of from 0.5 to 100% by weight, based on the amount of dibenzyl ether.

19. A process according to claim 3 wherein one or more acidic ion exchangers selected from the group consisting of optionally fluorinated, sulfonylated polystyrenes, optionally fluorinated or perfluorinated, sulfonylated styrene-divinylbenzene copolymers, and optionally fluorinated or perfluorinated sulfonylated phenol-formaldehyde resins are arranged as a fixed bed and used with space velocities of from 1.0 to 3000 g of dibenzyl ether per liter of ion exchanger per hour.

20. A process according to claim 6 wherein one or more heteropolyacids are used as a suspended catalyst in an amount of from 0.05 to 100% by weight, based on the amount of dibenzyl ether.

21. A process according to claim 6 wherein one or more heteropolyacids are used as a fixed bed with space velocities of from 1.0 to 3000 g of dibenzyl ether per liter of heterogenized heteropolyacid per hour.

* * * * *